United States Patent [19]

Bonnem

[11] Patent Number: 4,846,782
[45] Date of Patent: Jul. 11, 1989

[54] TREATMENT OF CANCER WITH INTERFERON AND RADIOTHERAPY

[75] Inventor: Eric Bonnem, Plainfield, N.J.

[73] Assignee: Schering Corporation, Kenilworth, N.J.

[21] Appl. No.: 125,429

[22] Filed: Nov. 25, 1987

Related U.S. Application Data

[63] Continuation of Ser. No. 839,679, Mar. 14, 1986, abandoned.

[51] Int. Cl.$^4$ ............................................. A61N 5/12
[52] U.S. Cl. ........................................ 600/1; 424/85.7
[58] Field of Search .................... 424/85.7; 600/1, 3–5

[56] References Cited

U.S. PATENT DOCUMENTS

| | | | |
|---|---|---|---|
| 4,499,072 | 2/1985 | Sunkara et al. | 424/85 |
| 4,559,228 | 12/1985 | de la Torre | 424/95 |
| 4,622,952 | 11/1986 | Gordon | 128/1.3 |

FOREIGN PATENT DOCUMENTS 32134  7/1981  European Pat. Off. .

OTHER PUBLICATIONS

Dritschilo et al., Am. J. Clinic, Onc. 5, 79, (1982).
Namba et al., Cancer 54, 2262, (1984).
Gould et al., J. Interferon Research 4, 123, (1984).
Nederman et al., Acta Radiologica Oncology, 21, 231, (1982).
Lvovsky et al., Int. J. Rad. Onc. Bio. Phys. 11, 1721, (1985).
Mahaley et al., J. Bio. Resp. Modifiers 3, 19, (1984).
Capero et al., Abstracts 2nd Cuban Seminar Interferon Biotechnol., (Feb. 20–22, 1986), pp. 01–267.
Holsti et al., Abstracts Ann. Mtg. Interferon System (TNO/ISIR), Clearwater Beach, Fla., p. 141, (Oct. 13–18) 1985.
Torrisi et al., Int. J. Radiat. Oncol., Biol. Phys. 12, 1453–1456, (1986).
Gresser, Becker editor, Cancer-A Comprehensive Treatise 5, 521–71, (1977), Plenum press.
Real, et al., J. Biol. Resp. Modif., 4, 141–146, (1985).
Mattson et al., J. Biol. Resp. Modif., 4, 8–17, (1985).
Nagata et al., Nature, 284, 316, (1980).
Mattson et al, Biol. Interferon System, Kirchner et al editors 531, 540, (1985), Elsevier Science Publishers.
Mattson et al., European J. of Respiratory Dis. Suppl. 126, vol. 64, p. 572, (1983).
Mchaley, Jr. et al., "Immunobiology of Primary Intracranial Tumors", in *J. Neurosurgery*, vol. 63, Nov. 1985, pp. 719–725.
Kadish et al., "Natural Cytotoxicity in Patients Undergoing Radiation Therapy", in *Am. J. Clin. Oncol. (CCT)*, 6:53–59, 1983.
Miloff et al., "Recombinant Leukocyte Alpha Interferon in Advanced Ovarian Carcinoma", in Cancer Treatment Reports, vol. 69, No. 7–8, Jul./Aug. 1985.
Favalli et al., "Modulation of Natural Killer Activity by Thymosin Alpha 1 and Interferan"in *Cancer Immnol. Immunother*, (1985), 20: 189–912.
Aebersold et al., "Effects of Interferon and Radiation Dose on the Suppressive Activity of Human Lymphocytes Primed with Allogeric Cells in Mixed Lymphocyte Cultures" in *Journal of Biological Response Modifiers*, vol. 4, 1985, pp. 251–257.
Lenzhofer R. et al., "Recombinant Human IFN Alpha 2, (RHV–IFN–Alpha 2), in Advanced Breast Cancer" in *Drugs Exptl. Clin. Res.* X(7), 463–470, (1984).

*Primary Examiner*—C. Fred Rosenbaum
*Assistant Examiner*—Mark F. Colosimo
*Attorney, Agent, or Firm*—Gerald S. Rosen; Thomas D. Hoffman

[57] ABSTRACT

Radiation sensitive human cancers are treated with combined interferon and radiation therapy.

1 Claim, No Drawings

TREATMENT OF CANCER WITH INTERFERON AND RADIOTHERAPY

This is a continuation, of application Ser. No. 839,679 filed Mar. 14, 1986 now abandoned.

BACKGROUND OF THE INVENTION

The interferons represent a group of biologically active glycoproteins with proven anti-viral and anti-neoplastic properties. Several subtypes of interferon have been defined based upon differences in antigenic and biological properties. The interferon subtypes are alpha interferon, beta interferon and gamma interferon.

Advances in biotechnical research in the past 10 years have resulted in the production of highly purified recombinant DNA interferons.

Clinical studies have shown that when used as a single agent, the interferons have antitumor activity in e.g. renal cell carcinoma, melanoma, indolent forms of non-Hodgkin's lymphoma, Kaposi's sarcoma and hairy cell leukemia. Other tumors including ovarian carcinoma and glioblastoma multiforme appeared to be less responsive to interferon. All subtypes of interferon are not active against all the listed tumors.

Radiation therapy is a mainstay in modern cancer treatment with proven efficacy in many human tumors. There is, however, always a need for continued improvement in effectiveness of such treatment. Among the attempts to improve the efficacy of radiation treatment are efforts to develop radiation sensitizers or potentiators which enable the radiation to cause increased tumor destruction. Despite numerous laboratory and clinical studies, no single agent has, to date, emerged as the optimal radiation sensitizer.

There have been a small number of studies in the laboratory involving interferon and radiation therapy, however, the results were inconclusive.

Dritschilo et al., Am. J. Clinic. Onc. 5 79 (1982) studied the effect on IFN on the radiation response of mouse 3T3 cells in tissue culture. A species specific enhancement of radiation killing of 3T3 cells irradiated in the presence of mouse L-cell interferon was observed as a reduction in the shoulder portion of the cell survival curve. Split-dose experiments designed to test for changes in sub-lethal radiation injury repair failed to demonstrate an inhibitory interferon effect. Dritschilo et al., postulate that interferon potentiates radiation injury possibly by inhibiting the ability of the cultured cells to accumulate sub-lethal radiation injury.

Namba et al., Cancer 54, 2262 (1984) confirmed the Dritschilo et al., observations in a study of the combined use of interferon and radiation therapy using HeLa cells.

Gould et al., J. Interferon Research 4 123 (1984) observed in vitro radiosensitization of human bronchogenic carcinoma with beta interferon but not with alpha interferon. Gould et al. noted that the degree of radiosensitization of the various interferons paralleled their anti-proliferative effects when used alone on the bronchogenic cell lines. Nevertheless, Gould et al. concluded that the ant-neoplastic effects of the combined use of interferon and radiation were supra-additive indicating radiosensitization.

Nederman et al., Acta Radiologica Oncology, 21, 231 (1982) observed enhanced growth retardation in human glioma cell cultures following combined therapy in comparison to interferon and radiotherapy used alone. Nederman et al. attributes their results to the additive antineoplastic effect of the radiation and interferon but could not confirm radiosensitization.

Combined radiation and interferon studies have not been reported in animal model systems, primarily because of the species specificity of interferon; Lvovsky et al., Int. J. Rad. Onc. Bio. Phys. 11, 1721 (1985) observed enhanced tumor control using the interferon inducer, poly ICLC and radiation, and radiation in the mouse Lewis lung tumor model. A delay in tumor regrowth and a prolonged duration of survival were observed in the inducer plus radiation animals as compared to either inducer or radiation alone.

Mahaley et al., J. Bio. Res. Modifiers 3 19 (1984) reported a phase I study of the combined use of interferon and radiation therapy in nine patients with anaplastic glioma following subtotal resection. Patient survival was comparable to that for a matched group with combined BCNU and radiation therapy. Other reports show unexpected increases in toxicity when combined therapy is used.

Real et al., J. Bio. Resp. Modifiers, 4,141 (1985) reported severe oral cavity mucositis in two patients with Daposi's sarcoma requiring cessation of radiotherapy.

Mattson et al., J. Biol. Resp. Modifiers 4, 8–17 (1985) reported that the concomitant use of interferon and radiotherapy has been associated with an increased incidence of radiation pneumonitis in patients with small cell carcinoma.

SUMMARY OF THE INVENTION

This invention relates to a method of treating radiation sensitive human cancers such as carcinomas and sarcomas by concomitantly administering radiation with an interferon radiation sensitizer.

The method comprises administering to a patient with a radiation sensitive cancer sufficient amount of an interferon radiation sensitizer to effectively sensitize the cancer to radiation, then administer radiation in standard amounts.

As used herein "interferon" includes natural and recombinant alpha (leucocyte) and beta (fibroblast) interferons, but alpha interferons are preferred. As used herein, "alpha interferon" means a natural or recombinant interferon exhibiting biological properties similar to those of human leucocyte interferon. A number of alpha species are known which are usually designated by a numeral after the Greek letter designation, and all are contemplated for use in this invention as radiation sensitizers. Preferred forms of alpha interferon for use in this invention are alpha-1 and alpha-2 interferons. Particularly preferred is alpha-2 interferon and most preferred is alpha-2 interferon prepared by recombinant-DNA methods, the so-called recombinant-DNA alpha-2 interferon.

Recombinant-DNA alpha-2 interferon may be prepared, for example, as disclosed by Nagata et al., Nature, 284, 316 (1980) and in European patent 32,134.

DETAILED DESCRIPTION

This invention provides a method for concomitantly treating radiation sensitive cancers such as sarcomas and carcinomas with radiation sensitizing interferon and standard radiation in a regimen which requires shorter radiation treatment times, thus ameliorating side effects ordinarily associated with radiation treatment.

The invention will hereafter be described using as an example the preferred recombinant DNA alpha-2 interferon, designated IFN.

I have found that three-times-per-week administration of from $2 \times 10^6$ to $5 \times 10^6$ International Units of IFN per square meter followed by administration of standard amounts of radiation to a patient with a radiation sensitive cancer is well tolerated and results in reduction and elimination of tumors.

The preferred mode of administration of IFN is by injection, preferably subcutaneously, administered approximately two hours before radiation.

The radiation is administered according to this invention by standard techniques with standard megavoltage equipment, such as AECL Theratron 80, Varian Clinac 4 or Varian Clinac. The maximum size of the radiation portal should be no greater than 300 cm². A suitable does is between about 15 Gy and 35 Gy, with the specific dose dependent on the area of the body treated. Thus, a dose to the spinal cord would be about 35 Gy, whereas a dose to the bilateral kidneys would be about 15 Gy and to the whole liver 20 Gy. Breaks in the therapy are at the discretion of the clinician taking into consideration the patients tolerance for radiation therapy.

The injectable compositions of IFN are made by conventional means. Thus, they can be made with sterile distilled water or buffered solutions and the like containing, e.g. preservatives.

Tests in the clinic demonstrating this invention were conducted as follows:

METHODS AND MATERIALS

Patient Population

Sixteen patients were enrolled in the study of the combined use of alpha-2 recombinant interferon and radiation therapy conducted at the Georgetown University Hospital. Patients were declared eligible for participation if they had histological confirmation of an advanced unresectable or metastatic carcinoma or sarcoma and a life expectancy of at least three months.

Of the 16 patients, 8 were male. The mean age was 61 years with a range of 43 to 76. Fifteen of the 16 patients had histological diagnosis of epithelial carcinoma with primaries located in the lung, esophagus, pancreas, cervix, and kidney. One patient had bony metastasis and a soft tissue mass secondary to multiple myeloma. Of the 16 patients, 14 are available for anaylsis. Two patients were declared inevaluable because they were unable to complete the radiotherapeutic course. All patients were removed from prior hormonal therapy or chemotherapy two to four weeks prior to beginning the protocol.

Study Design

Prior to enrollment, all patients were throughly examined and their disease clinically staged using chest x-rays, computerized tomography, EKG, hematologic and blood chemistries. Clotting studies including total fibrinogen determination, PTT, PT, TT, and fibrin degradation products, were conducted. Theraftater, each patient was sequentially assigned to groups consisting of six subjects each which was then further subdivided into two subgroups of three patients each (Subgroups A and B). Each group of six patients received the same dose of alpha-2-interferon which was escalated in each succeeding group. The doses studied were $2.0 \times 10^6$ IU/m² and $5.0 \times 10^6$ IU/m². Doses higher than $5.0 \times 10^6$ IU/m² were not used because they are toxic. Within a given group, one subgroup (Subgroup A) received the given interferon dose subcutaneously five times per week on conjunction with the radiotherapy. The remaining subgroup (Subgroup B) received the same IFN dose subcutaneously three times per week (M,W,F). The daily dose of interferon was administered two hours prior to radiation therapy in order to allow for adequate serum levels at the time of radiation administration. The combined usage of interferon and radiation was continued unless interrupted by significant treatment toxicity or patient resignation from the protocol.

The interferon dosage was adjusted in the event of granulocytopenia less than 1500 cells per mm² depending on the platelet count with reduction in dosages ranging form 15 to 25%. interferon administration was temporarily stopped in all cases involving a granulocytopenia count of less than 1000 or a platelet count of less than 50,000. Administration of interferon was resumed when the involved patient showed evidence of hematologic recovery. Radiation therapy was administered using standard radiation technique and megavoltage equipment (AECL Theratron 80, Varian Clinac 4 or Varian Clinac 18). All fields were simulated and "shrinking field technique" was used, when possible in accordance with established radiotherapeutic priniciples. The maximum size of the radiation portal was limited to 300 cm² with appropriate shielding to surrounding normal tissue using individually manufactured blocks. The dose to the spinal cord was limited to 35 Gy, to the whole liver to 20 Gy, and to the bilateral kidneys 15 Gy, respectively. Radiotherapeutic breaks in treatment lasting at least one week were instituted at the discretion of the radiotherapist in accordance with the patient's overall tolerance to treatment.

Toxicity Evaluation and Response Criteria

Each patient was vigorously monitored for early signs of toxicity as well as radiographic evidence of clinical effectiveness throughout the treatment course and on a regular basis thereafter. Methods of evaluation included frequent physician examination, a regular scheduled performance of laboratory procedures including hematologic, serum chemical, and clotting studies. Radiographic studies included chest x-rays and CT scans as appropriate. Toxicity was graded in accordance with the Work Health Organization's recommendations for grading of acute and subacute toxicity. Performance status was graded from zero to four with complete disability being defined as four. Tumor response was determined by means of serial radiographic studies. Areas of referenced tumors were determined by multiplication of the longest diameter by the greatest perpendicular diameter. Complete response was then defined as the disappearance of all measurable disease determined by observation separated by at least four weeks with the appearance of no new lesions within the radiation portal. Partial response was a 50% decrease in the referenced tumor mass and stable disease was defined as a less than 50% decrease in tumor size, or less than 25% increase. A tumor growth larger than 25% was declared progressive disease.

Results

No specific differences in patient tolerance was noted at IFN doses between $2 \times 10^6$ and $5 \times 10^6$ IU/m². The three-day-per-week regimen was better tolerated as evidenced by treatment related toxic side effects and the ability of the patients to complete the planned irradiation course. The treatment related toxic side effects in the patients on the five-day-a-week regimen resulted in unsatisfactory patient tolerance of both IFN and radiation therapy.

The patients on the tri-weekly regimen were able to tolerate 100% of the planned dosage of IFN and 86% of the planned radiation treatment dose, whereas the patients on the five days per week regimen were able to tolerate only 22% of the originally planned IFN dosage and only 44% of the planned radiation treatment dosage.

Tumor response was determined one month following completion of therapy. Complete and partial responses were observed in six patients and no change was observed in eight patients. No patients had tumor progression.

Thus, the results of the clinical study indicate that the combined IFN and radiation therapy approach is feasible. Maximum tolerated dose and schedule of recombinant DNA alpha-2-interferon given subcutaneously in conjunction with daily radiation was three-times-per-week at $5.0 \times 10^6$ IU/m². This is superior to daily administration of IFN in conjunction with daily radiation treatment.

I claim:

1. A method of treating radiation sensitive human cancers in patients in need of such treatment which comprises administering subcutaneously to such patients between $2.0 \times 10^6$ IU/m² and $5.0 \times 10^6$ IU/m² of recombinant DNA-alpha-2-interferon three days a week at a time on those days prior to radiation therapy wherein radiation doses of from 15 to 35 Gy are administered five days a week including those days on which interferon is administered.

* * * * *